United States Patent [19]

Grivsky

[11] 4,179,524
[45] Dec. 18, 1979

[54] BIOLOGICALLY ACTIVE AMIDE

[75] Inventor: Eugene M. Grivsky, Chapel Hill, N.C.

[73] Assignee: Burroughs Wellcome Co., Research Triangle Park, N.C.

[21] Appl. No.: 916,276

[22] Filed: Jun. 16, 1978

[51] Int. Cl.² .................. A61K 31/165; C07D 239/64
[52] U.S. Cl. ................................ 424/324; 260/558 R
[58] Field of Search ..................... 424/324; 260/558 R

[56] References Cited
U.S. PATENT DOCUMENTS 4,041,071  8/1977  Grivsky ........................... 260/558 R

OTHER PUBLICATIONS

Chem. Abst. 78-29282Q (1973), also 9th Coll. Index. Chem. Sub. Praseodymium-2-Propenenitrile, p. 31782 cs.

Primary Examiner—Stanley J. Friedman
Attorney, Agent, or Firm—Donald Brown

[57] ABSTRACT

This application discloses the compound trans-3-fluoro-N-allylcinnamamide the use thereof as an anticonvulsant and a pharmaceutical preparation thereof which includes the compound or a pharmaceutically acceptable salt thereof.

17 Claims, No Drawings

BIOLOGICALLY ACTIVE AMIDE

This invention is concerned with chemicals which have valuable pharmacological properties. In particular, the invention concerns cinnamamides, their synthesis, pharmaceutical preparations containing them, and their use in medicine.

It has been found that the trans cinnamamide of formula (I), as defined below, have anti-convulsant activity in mammals as is shown by its effect upon mice when administered to them in established pharmacological tests. These tests are:
1. Maximal Electroshock Test (MES) in mice, a method described by Woodbury and Davenport, Arch int. Pharmacodyn. Ther. 92. P. 97–107 (1952).
2. Metrazol Seizure Test (MET) in mice, a method described by Swinyard, Brown and Goodman, J. Pharmacol. Exp. Therap. 106, 319–330 (1952).

In formula (I)

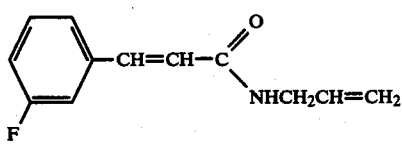

The compound of formula (I) may be made by any method known for the synthesis of cinnamamides of analogous structure. For example it may be prepared by the acylation of allylamine—by the corresponding acid of formula (II): m-F-PhCH=CHCO$_2$H—or a reactive derivative thereof such as a thioester or an ester (e.g. an alkyl ester or thioester where the alkyl has e.g. 1 to 4 carbon atoms), an amide, an acid halide (e.g. an acid chloride) or an acid anhydride. A wide variety of reaction conditions may be employed depending upon the nature of the acylating agent, but in general the reactants may be refluxed together, preferably in an inert liquid medium such as ether, benzene, toluene or cyclohexane.

A most convenient method of synthesis is to react the acid chloride with the appropriate amine. Preferably one equivalent of the halide should be used with two or more equivalents of the amine, but the molar excess of the amine may be replaced by another base such as triethylamine, pyridine, dimethylaniline, or potassium or sodium carbonate. A wide variety of polar or nonpolar liquid media may be used including water, alkanols such as methanol, ethanol, etc., ether, dioxane, benzene, toluene, xylene, petroleum ether, cyclohexane, tetrahydrofuran, chloroform and carbon tetrachloride. A wide range of temperature conditions may be employed, for example from −10° C. to the reflux temperature of the reaction mixture.

The compound of formula (I) may be further prepared directly from the corresponding alcohol or aldehyde of formula (III) and (IV) at a temperature below 10° C.

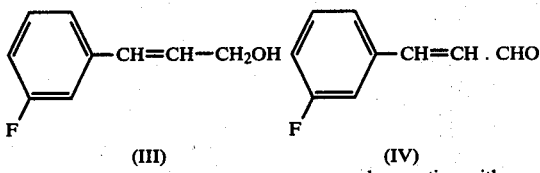

by reaction with allylamine in the presence of nickel peroxide and an inert liquid medium such as ether, benzene, tetrahydrofuran, or a petroleum hydrocarbon.

The compound of formula (I) may also be made by the reaction of an amide of formula (V): R.NH.W wherein W is a leaving group, for example —CO.H (a formamide), —CO.alkyl where the alkyl has eg. 1 to 4 carbon atoms (an amide), —CONH$_2$ (urea), —COO.alkyl (urethane having 1–4 carbon atoms in the alkyl group) and R in allyl, with the acid of formula (II) or a reactive derivative thereof, for example the acid anhydride or halide. When the anhydride is used, a catalytic amount of sulphuric acid is preferably included. The reactants are conveniently heated together in a liquid medium.

In a further method for making a compound of formula (I), water, a hydrogen halide or molecular halogen is eliminated from a compound of formula (VI)

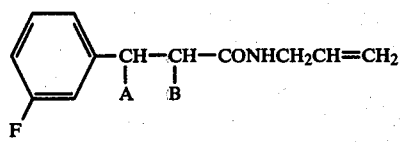

wherein A and B are the same and each is halo or one of A and B is halo or hydroxy and the other is hydrogen.

For example, the elimination of water from the α- or β-hydroxy compounds of formula (VI) may be effected by reaction with a dehydrating agent such as a base (eg. aqueous sodium hydroxide) or concentrated sulphuric or polyphosphoric acid. The monohalo intermediates may be treated with a base (eg. potassium hydroxide or dimethylaniline) or merely heated to release the hydrogen halide. The dihalo intermediates may be reduced, for example with zinc and ethanol or converted to the diiodo compounds by treatment with potassium iodide with subsequent release of molecular iodine.

The intermediate acid of formula (II) may be made by classical organic synthetic methods such as the Perkin synthesis, the Reformatsky reaction and the Knoevenagel condensation.

The compound of formula (I) may be used for the treatment or prophylaxis of convulsions of mammals such as mice, dogs and cats, more importantly of man. In particular it may be used in the treatment of grand mal, petit mal, psychomotor epilepsy and focal seizures at a dose of 2 to 200 mg/kg of body weight per day. The optimum dose of course will vary with the condition of the patient and the route of administration, but the preferred dose is in the range of 20 to 60 mg/kg, most conveniently 30 to 50 mg/kg body weight, per day. Administration of the desired daily dose is preferably in three divided doses. For example, convenient forms of administration include tablets each containing from 100 to 500 mg of a compound of formula (I).

For use in medicine the compound of formula (I) may be administered as a pure chemical but is preferably presented with an acceptable carrier therefor as a pharmaceutical composition. The carrier must of course be 'acceptable' in the sense of being compatible with the other ingredients of the composition and not deleterious to the recipient of the composition. The carrier may be a solid or a liquid or a mixture of solid and liquid substances, and is preferably formulated with a compound of formula (I) as a unit-dose composition, for example a tablet, capsule or sachet for oral administration or a suppository for rectal administration. Other pharmaceutically active substances may also be present in compositions of the present invention, and the composition may be formulated by any of the well-known techniques of pharmacy consisting basically of admixture of its components. Unit-dose compositions, for oral, rectal or parenteral administration (vid. inf.), conveniently contain a compound of formula (I) in an amount in the range 100 to 500 mg.

For oral administration, fine powders or granules of the compounds may contain diluents and dispersing and surface active agents, and may be presented in a draught in water or in a syrup; in capsules or cachets in the dry state or in an aqueous or non-aqueous suspension, when a suspending agent may also be included; in tablets, preferably made from granula of the active ingredient with a diluent, by compression with binders and lubricants; or in a suspension in water or a syrup or an oil or in a water/oil emulsion, when flavouring, preserving, suspending, thickening and emulsifying agents may also be included. The granules or the tablets may be coated, and the tablets may be scored.

For parenteral administration (by intramuscular or intraperitoneal injection), the compounds may be presented in unit dose or multi-dose containers in aqueous or non-aqueous injection solutions which may contain antioxidants, buffers, bacteriostats and solutes which render the compounds isotonic with the blood; or in aqueous or non-aqueous suspensions when suspending agents and thickening agents may also be included; extemporaneous injection solutions and suspensions may be made from sterile powders, granules or tablets which may contain diluents, dispersing and surface active agents, binders and lubricants.

It will be understood from the foregoing description that what we will claim in accordance with this invention comprises any novel feature described herein, principally but not exclusively as follows:

(a) Novel compound of formula (I) hereinabove defined.

(b) Novel compound of formula (I) hereinabove defined having the trans configuration.

(c) The synthesis of the novel compound of formula (I) by any known method and in particular the methods specifically described above and including the reaction of an acid m-F-PhCh=CHCO$_2$H or a reactive derivative thereof with a compound of the formula R.NH.W wherein W is a leaving group and R is allyl.

(d) A pharmaceutical composition comprising a compound of formula (I) and a pharmaceutically acceptable carrier therefor.

(e) A method for the treatment or prophylaxis of convulsions of a mammal comprising the administration to the mammal of an anti-convulsant effective, non-toxic amount of a compound of formula (I).

The following Examples illustrate the present invention but should not be construed as in any way constituting a limitation thereof. All temperatures are in degrees Celsius.

EXAMPLE 1—Trans 3-Fluoro-N-allylcinnamamide

A solution of 3-fluorocinnamoyl chloride (3.7 g) in dry toluene (35 ml) was added with stirring to allylamine (8 ml) in dry benzene (100 ml). The reaction mixture was allowed to stand at room temperature for three days. After evaporation of the solvents under reduced pressure the residue was triturated with water containing a small amount of sodium carbonate and washed with water. Recrystallization from ethanol: water gave 3-fluoro-N-allylcinnamamide (3.3 g), m.p. 84.5-87° C. as fine white needles. Elemental analysis, nmr and ir spectra were consistent with the structure assignment.

EXAMPLE 2—Tablet

A compressed tablet is prepared from the following ingredients:
Trans 3-fluoro-N-allylcinnamamide—300 mg
Starch, corn—50 mg
Microcrystalline cellulose—50 mg
Stearic acid—4 mg
Magnesium stearate—1 mg
Fused silica—1 mg EXAMPLE 3 Capsule A gelatin capsule is filled with the following ingredients:
Trans 3-fluoro-N-allylcinnamamide—300 mg
Lactose—75 mg
Starch, corn—20 mg
Fused silica—2 mg
Magnesium stearate—3 mg EXAMPLE 4—Suppository A suppository is formulated from the following ingredients:
Trans 3-fluoro-N-allylcinnamamide—300 mg
Cocoa butter—2000 mg EXAMPLE 5—Suspension A syrup suspension is prepared from the following ingredients:
Trans 3-fluoro-N-allylcinnamamide—300 mg
Sodium carboxymethylcellulose—20 mg
Microcrystalline cellulose—100 mg
Glycerin—500 mg
Polysorbate 80—0.1 ml
Flavoring agent—q.s.
Preserving agent—0.1%
Sucrose syrup—q.s. to 5 ml

EXAMPLE 6

In the MES pharmacological test referred to hereinbefore, trans 3-fluoro-N-allylcinnamamide had an ED$_{50}$ (i.p.) in mice of 50 mg/kg.

EXAMPLE 7

Trans 3-fluorocinnamoyl chloride

A mixture of trans 3-fluorocinnamic acid (32.3 g), thionyl chloride (48 g) and dry benzene (300 ml) was heated at reflux for 2 hours. Solvent and excess thionyl chloride was removed by distillation at reduced pressure leaving trans 3-fluorocinnamoyl chloride (34 g) as the oil.

I claim:

1. Trans-3-fluoro-N-allylcinnamamide

2. A pharmaceutical composition for use as an anticonvulsant comprising an effective non-toxic anticonvulsant amount of the compound trans-3-fluoro-N-allyl-cinnamamide and a pharmaceutically acceptable carrier therefore.

3. The composition of claim 2 in which the carrier is a solid or liquid.

4. The composition of claim 2 which is suitable for parenteral or rectal administration.

5. The composition of claim 2 which is suitable for oral administration.

6. The composition of claims 2, 3, 4, or 5 in which the amount is 100 to 500 mg.

7. The composition of claim 2 or 3 in the form of a tablet.

8. The composition of claim 7 in which the amount is 100 to 500 mg.

9. The method of treatment on prophylaxis of convulsions in a mammal comprising the administration to the mammal of an anticonvulsant effective non toxic amount of the compound trans-3-fluoro-N-allylcinnamamide.

10. The method of claim 9 in which the mammal is a human.

11. The method of claim 9 or 10 in which the compound is administered orally.

12. The method of claim 9 or 10 in which the compound is administered parenterally.

13. The method of claim 9 or 10 in which the amount administered is 2 to 200 mg/kg per day.

14. The method of claim 11 in which the amount administered is 2 to 200 mg/kg per day.

15. The method of claim 12 in which the amount administered is 2 to 200 mg/kg per day.

16. The method of claims 9, 10, 14, or 15 in which the amount administered is 20 to 60 mg/kg per day.

17. The methods of claims 9, 10, 14, or 15 in which the amount administered is 30 to 50 mg/kg per day.

* * * * *